US009820994B2

(12) United States Patent
Campos Perez et al.

(10) Patent No.: US 9,820,994 B2
(45) Date of Patent: Nov. 21, 2017

(54) CERCLAGE PESSARY CONTAINING PROGESTERONE OF PROLONGED, SUSTAINED, AND CONTINUOUS RELEASE USEFUL FOR PREVENTION OF PRETERM BIRTH

(71) Applicant: Laboratorios Andromaco S.A., Santiago (CL)

(72) Inventors: German Arzobindo Campos Perez, Valdivia (CL); Shu-Chen Chen, Santiago (CL)

(73) Assignee: LABORATORIOS ANDROMACO S.A. (CL)

( * ) Notice: Subject to any disclaimer, the term of this patent is extended or adjusted under 35 U.S.C. 154(b) by 74 days.

(21) Appl. No.: 14/405,037

(22) PCT Filed: Jun. 28, 2014

(86) PCT No.: PCT/IB2014/062691
§ 371 (c)(1),
(2) Date: Dec. 2, 2014

(87) PCT Pub. No.: WO2015/198104
PCT Pub. Date: Dec. 30, 2015

(65) Prior Publication Data
US 2016/0250229 A1    Sep. 1, 2016

(51) Int. Cl.
*A61F 6/14*    (2006.01)
*A61K 31/56*    (2006.01)
(Continued)

(52) U.S. Cl.
CPC .............. *A61K 31/573* (2013.01); *A61F 6/08* (2013.01)

(58) Field of Classification Search
CPC .............................. A61K 9/0036; A61K 31/57
(Continued)

(56) References Cited

U.S. PATENT DOCUMENTS 415,991 A    11/1889    Zipernowsky
5,869,081 A    2/1999    Jackanicz et al.
(Continued)

FOREIGN PATENT DOCUMENTS

DE    102012009057 A1    11/2013
WO    99/22680 A1    5/1999
(Continued)

OTHER PUBLICATIONS

NuSil XL-103 Safty Data Sheet 2013.*
(Continued)

*Primary Examiner* — Shengjun Wang
(74) *Attorney, Agent, or Firm* — J.A. Lindeman & Co., PLLC

(57) ABSTRACT

Cerclage pessary containing progesterone homogeneously distributed in the pessary body providing a prolonged, sustained and continuous release for a period of at least 6 months, wherein the pessary consists of dimethylsiloxane elastomer with RTV (Room Temperature Vulcanization) mechanism, the progesterone amount is from 20% to 30% w/w, relative to pessary weight and the ratios of the polymers forming the matrix is from 6:1 to 14 1. The cerclage pessary is useful for the prevention of preterm birth. Progesterone diffuses through the polymer continuously, without altering the shape and integrity of the pessary, since the elastomer forming the polymeric matrix used herein is not biodegradable. This guarantees that the form of pessary remains intact until the end of treatment.

12 Claims, 7 Drawing Sheets

(51) Int. Cl.
 A61F 6/06 (2006.01)
 A61K 31/573 (2006.01)
 A61F 6/08 (2006.01)
(58) Field of Classification Search
 USPC .................................. 424/432, 430; 514/177
 See application file for complete search history.

(56) References Cited

U.S. PATENT DOCUMENTS

| | | | |
|---|---|---|---|
| 2004/0089308 A1 | 5/2004 | Welch | |
| 2008/0248017 A1 | 10/2008 | Ron et al. | |
| 2009/0202612 A1* | 8/2009 | Ahmed | A61F 6/08 424/432 |
| 2009/0264395 A1* | 10/2009 | Creasy | A61K 31/57 514/177 |
| 2012/0093911 A1* | 4/2012 | Malcolm | A61K 9/0036 424/433 |

FOREIGN PATENT DOCUMENTS

| | | |
|---|---|---|
| WO | 2006010097 A2 | 1/2006 |
| WO | 2009099586 A2 | 8/2009 |
| WO | 2011011099 A1 | 1/2011 |
| WO | 2012170578 A1 | 12/2012 |

OTHER PUBLICATIONS

Z. Alfirevic, et al; Vaginal progesterone, cerclage or cervical pessary for preventing preterm birth in . . . ; Ultrasound Obstet. Gynecol., 2013; vol. 41; pp. 146-151.
B. Arabin, et al; Is treatment with vaginal pessaries an option in patients with a sonographically detected short cervix?; J. Perinat. Med., 2003; vol. 31; pp. 122-133.
B. Arabin, et al; Comparison of transvaginal sonography in recumbent and standing maternal positions to predict spontaneous . . . ; Ultrasound Obstet. Gynecol., 2006; vol. 27; pp. 377-386.
B. Arabin, et al; Cervical pessaries for prevention of spontaneous preterm birth: past, present and future; Ultrasound Obstet. Gynecol., 2013; vol. 42; pp. 390-399.
S. Astle, et al; The involvement of progesterone in the onset of human labour; European Journal of Obstetrics & Gynecology and Reproductive Biology; 2003; vol. 108; pp. 177-181.
V. Berghella, et al; Ultrasound assessment of the cervix; Clinical Obstetrics and Gynecology; 2003; vol. 46; No. 4; pp. 947-962.
V. Berghella; Novel developments on cervical length screening and progesterone for preventing preterm birth; The Author Journal Compilation; 2008; pp. 182-187.
S. Campbell; Universal cervical-length screening and vaginal progesterone prevents early preterm births, reduces . . . ; Ultrasound Obstet. Gynecol., 2011; vol. 38; pp. 1-9.
M.M. Cannie, et al; Arabin cervical pessary in women at high risk of preterm birth: a magnetic resonance . . . ; Ultrasound Obstet. Gynecol., 2013; vol. 42; pp. 426-433.
S. Caritis; Cervical pessary use and preterm birth: how little we know; The Lancet.com; 2012; pp. 1-2.
C. Celik, et al; Cervical length and obstetric history predict spontaneous preterm birth: development and validation . . . ; Ultrasound Obstet. Gynecol., 2008; vol. 31; pp. 549-554.
A. Conde-Agudelo, et al; Vaginal progesterone versus cervical cerclage for the prevention of preterm birth in women . . . ; Am. J. Obstet Gynecol.; 2013; vol. 208(1); pp. 1-29.
R.G. Cross; Treatment of habitual abortion due to cervical incompetence; Letters to the Editor; 1959; p. 127.
E.B. Fonseca, et al; Progesterone and the risk of preterm birth among women with a short cervix; The New England Journal of Medicine; 2007; vol. 357; pp. 462-469.

E.A. DeFranco, et al; Vaginal progesterone is associated with a decrease in risk for early preterm birth and improved . . . ; Ultrasound Obstet. Gynecol., 2007; vol. 30; pp. 697-705.
J.M. Dodd, et al; Progesterone supplementation for preventing preterm birth: a systematic review and meta-analysis; Acta Obstet Gynecol. Scand, 2005; vol. 84; pp. 526-533.
E.S. Draper, et al; Prediction of survival for preterm births by weight and gestational age: restrospective . . . ; BMJ; 1999; vol. 319; pp. 1093-1097.
R.L. Goldenberg, et al; The preterm prediction study: risk factors in twin gestations; Am. J. Obstet Gynecol; 1996; vol. 175; No. 4; pp. 1047-1053.
R.L. Goldenberg, et al; Preterm Birth 1—Epidemiology and causes of preterm birth; thelancet.com; 2008; vol. 371; pp. 75-84.
M. Goya, et al; Cervical pessary in pregnant women with a short cervix (PECEP): an open-label randomised controlled trial; thelancet.com; 2012; vol. 379; pp. 1800-1806.
E. Grazzini, et al; Inhibition of oxytocin receptor function by direct binding of progesterone; Letters to Nature; 1998; vol. 392; pp. 509-512.
S.S. Hassan, et al; Vaginal progesterone reduces the rate of preterm birth in women with a sonographic short cervix: a multicenter, . . . ; Ultrasound Obstet. Gynecol., 2011; vol. 38; pp. 18-31.
V.C.F. Heath, et al; Cervical length at 23 weeks of gestation: prediction of spontaneous preterm delivery; Ultrasound Obstet. Gynecol., 1998; vol. 12; pp. 312-317.
J.D. Iams, et al; The length of the cervix and the risk of spontaneous premature delivery; The New England Journal of Medicine; 1996; vol. 334; No. 9; pp. 567-572.
J.D. Iams, et al; Preterm Birth 2—Primary, secondary, and tertiary interventions to reduce the morbidity and mortality of preterm birth; thelancet.com; 2008; vol. 371; pp. 164-175.
G.S. Jayasooriya, et al; The use of progesterone and other progestational agents to prevent spontaneous preterm labour and preterm birth; Expert Opinion Pharmacother; 2009; vol. 10; No. 6; pp. 1007-1016.
N. Marlow, et al; Neurologic and developmental disability at six years of age after extremely preterm birth; The New England Journal of Medicine; 2005; vol. 352; No. 1; pp. 9-19.
J.A. Martin, et al; Births: Final data for 2002; National Vital Statistics Reports; 2003; vol. 52; No. 10; pp. 1-114.
R. Menon; Spontaneous preterm birth, a clinical dilemma: etiologic, pathophysiologic and genetic heterogeneities and racial disparity; Acta Obstet Gynecol Scand; 2008; vol. 87; No. 6; pp. 1.
J. Owen, et al; Mid-trimester endovaginal sonography in women at high risk for spontaneous preterm birth; American Med. Assoc.; 2001; vol. 286; No. 11; pp. 1340-1348.
R. Romero, et al; The role of cervical cerclage in obstetric practice: can the patient who could benefit from this procedure be identified?; Am. Journ. of Obst. and Gynecol.; 2006; vol. 194; pp. 1-9.
R. Romero, et al; Vaginal progesterone to reduce the rate of preterm birth and neonatal morbidity: a solution at last; Women's Health; 2011; vol. 7; No. 5; pp. 501-504.
S. Saigal, et al; Preterm Birth 3—An overview of mortality and sequelae of preterm birth from infancy to adulthood; thelancet.com; 2008; vol. 371; pp. 261-269.
R. Simcox, et al; A randomized controlled trial of cervical scanning vs history to determine cerclage in women at high risk of preterm birth (CIRCLE trial); Am. Journ. Obst & Gynecol; 2009; pp. 623.1-623.6.
A.P. Souka, et al; Cervical length at 23 weeks in twins in predicting spontaneous preterm delivery; Obst. & Gynecol; 1999; vol. 94; No. 3; pp. 450-454.
M.S. To, et al; Prediction of patient-specific risk of early preterm delivery using maternal history and sonographic . . . ; Ultrasound Obstet. Gynecol.; 2006; vol. 27; pp. 362-367.

* cited by examiner

CERCLAGE PESSARY CONTAINING PROGESTERONE OF PROLONGED, SUSTAINED, AND CONTINUOUS RELEASE USEFUL FOR PREVENTION OF PRETERM BIRTH

CROSS REFERENCE TO RELATED APPLICATION

This Application is a 371 of PCT/IB2014/062691 filed on Jun. 28, 2014, application which is incorporated herein by reference.

The present invention consists of a cervical pessary containing sustained release progesterone releasing the hormone continuously and steadily for a prolonged period of at least 6 months in an amount of 20 to 30 mg per day, useful for prevention of preterm birth.

STATE OF THE ART

Preterm birth, before 37 weeks of gestation, with an incidence of about 10%, is the most important cause of perinatal morbidity and mortality worldwide (Iams et al., 2008; Goldenberg et al., 2008; Draper et al., 1999). Preterm birth accounts for about 28% of neonatal deaths worldwide (Menon, 2008), being most critical between 32 and 36 weeks; in this period 1% of children born alive do not survive the first year of life (Martin et al., 2003). Mortality and morbidity are inversely related to gestational age and while advances in neonatal care have improved considerably, remains a significant risk of disability in extremely preterm surviving infants (Marlow et al., 2005; Saigal et al., 2008).

From the information available, it is known that preterm birth is not due to a single condition, so there is no just a single test for its prediction and even less a single intervention able to prevent preterm birth (Romero, 2011). One of the most important causes of risk of spontaneous preterm birth in singleton or twin pregnancy is a reduced length of the uterine cervix. A measurement by transvaginal ultrasound between 20-24 weeks of gestation, has emerged as an important antecedent to consider in identifying women who may have a spontaneous preterm birth (Iams J D et al., 1996; Celik E. et al., 2008; Owen J et al., 2001). It has been observed that the shorter cervical length, greater the risk of preterm delivery (V C Heath et al., 1998; Souka A P et al., 1999). When predicting preterm birth, also has to be considered the history of spontaneous preterm births and late miscarriages (Goldenberg R L et al., 1996; To M S et al., 2006).

Prevention of Preterm Birth

One of the strategies used in the prevention of preterm birth is the prophylactic administration of progesterone to women with a history of preterm birth and those with short cervix and singleton pregnancy in the middle of pregnancy. The mechanism of action of progesterone for preventing preterm birth appears to be related in one hand with a local anti-inflammatory effect that stops or slows down the cascade of biochemical events involved in cervical ripening, and secondly through a slight inhibitory effect over uterine contractions, maintaining, in this way, the uterus at rest (Jayasooriya et al 2009; Grazzini et al., 1998; Astle et al., 2003).

In published clinical studies (Da Fonseca E B et al., 2007; DeFranco E A et al., 2007; Hassan S S et al., 2011.) is described the use of different doses and routes of administration of progesterone for preventing preterm birth: 250 mg of progesterone IM weekly from 22 weeks; 200 mg daily of vaginal progesterone suppositories from 24 to 34 weeks; 90 mg of progesterone vaginal gel from 20 to 36 weeks. All the above, has shown an efficacy (rate of spontaneous preterm birth after 33 or 34 weeks) of approximately 40%.

The evidence derived from randomized clinical trials and meta-analysis reveals that vaginally administered progesterone is effective in preventing preterm birth in patients with short cervix (Campbell et al., 2011; Romero et al., 2011). However, even though it has been shown to significantly reduce the rate of spontaneous preterm birth (about 40-45% less) before 33-34 weeks, remains between 55-60% of patients with shortened cervix that, although progesterone, also give birth before 34 weeks (Dodd et al., 2005; Berghella, 2009; Hassan et al., 2011), which is consistent with the multi-causal nature of this condition (Romero and al, 2011).

Surgical cervical cerclage or Shirodkar or MacDonald cerclage, corresponding to a surgical procedure performed around the cervix, has also been proposed as an alternative of prevention in patients with single fetus pregnancy and short neck, but results in patients without prior history of cervical incompetence are still controversial, and is still under discussion which patients could really benefit from this treatment (Romero et al., 2006). A publication of Simcox et al. (2009) shows that the results in the prevention of preterm birth with cerclage indicated by short neck, is similar to the group that cerclage was indicated based on previous obstetric history, so waiting for cervical shortening to perform the procedure would not be justified. Moreover, the results of a meta-analysis of clinical studies concluded that vaginal progesterone as effective as cervical cerclage to reduce the rate of preterm birth in women with a singleton pregnancy with a history of premature birth and a short cervix<25 mm is (Conde-Agudelo et al., 2013).

An alternative to cerclage is the use of non-medicated cervical pessary, used to prevent preterm delivery since 1959. Theoretically, its effect is based on the mechanical ability it would have to move the cervix to the posterior region, slightly increasing neck length and changing the cervical angle, which reinforces the cervical canal and also reduces the chance of contacting membranes with vaginal environment, thus contributing to preserve its integrity (Caritis et al., 2012; Arabin et al., 2013). A study of Cannie et al. (2013) provided evidence that in singleton pregnancies with a short cervix, a cervical pessary delayed birth through a mechanical effect on uterine cervical angle; the measured angle was significantly more acute immediately after placing the pessary that prior to the placement, and remained unchanged until removal. This could avoid direct pressure on the membranes at the level of internal os and cervix itself. In consequence, uterine weight would increasingly be displaced toward the front lower uterine segment. In addition, the pessary can prevent opening of the internal os which is often associated with a dissociation of amnion and chorion, mainly in upright maternal position (Arabin et al., 2006). Normally an immature cervix in a pregnant woman is displaced posteriorly, towards the sacrum, with which intrauterine pressure and fetal presentation are exerted over the uterine segment and not over cervical internal os (Berghella et al., 2003) preventing its early dilatation. Another benefit of cervical pessary would be their contribution to maintaining the immunological barrier between the extra ovular chorioamniotic space and vaginal microbial flora, similar to the postulated mechanism for surgical cerclage. Cervical pessary is relatively noninvasive; not dependent on operator intervention and may be easily installed or removed without the use of anesthesia in an external medical center.

The silicone Arabin pessary is the most popular and is found in different sizes in diameter and height (pessary of Dr. Arabin—http://www.dr-arabin.de/e/intro.html). After installation, the patient is briefly observed to ensure that there is no discomfort, vaginal bleeding or uterine activity.

In a retrospective study of matched-paired analysis in women with twin pregnancies and cervical length below the 10 percentile by routine ultrasound, 23 cases were treated with pessary and 23 by expectant management. The rate of spontaneous birth before 32 weeks was 0% in the pessary group and 30% in controls (p<0.001). In the same study, 12 women with singleton pregnancies were treated with pessary and 12 by expectant management. The rate of spontaneous preterm delivery before 36 weeks was 0% in the pessary group and 50% in the control group (p<0.001) (Arabin B. et al 2003). In addition, in a multicenter study conducted in Spain 380 women, some with a history of preterm births and a cervix 25 mm, were randomly branched to the use of a cervical pessary or an expectant management. In the group that used pessary it was observed, compared to control group, a significant reduction in the rate of births under 34 weeks of gestation (6.3% vs 26.8%) and neonatal morbidity (4.2% vs 22.1%) respectively (Goya M et al., 2012). There are many other observational or case-control studies on the use of pessaries for the prevention of preterm delivery. These studies dating from 1959 had given promising results in the absence of severe adverse effects (Cross, 1959).

Alfirevic et al (2013) conducted an indirect comparison of the three interventions described above: 1) Administration of vaginal progesterone; 2) cerclage, and; 3) use of cervical pessary for preventing preterm birth in asymptomatic singleton pregnant women with a history of at least one previous birth at 34 weeks and cervical length less than 25 mm. The results indicate that the three strategies have similar effectiveness, no significant differences in the number of preterm births before 37 weeks among the three treatment groups was observed. However, the main result was that the use of cervical pessary had lower rates of preterm births before 34 weeks of gestation, which was statistically significant. In general, the rate of previous births at 34 weeks was close to 30% in the groups treated with progesterone or cerclage, compared with 12% of the group using the cervical pessary (Alfirevic et al., 2013).

In addition, the use of progesterone as a prophylactic measure to prevent preterm birth in women with a documented history of spontaneous preterm deliveries, is rapidly being accepted, although there is a need to identify the formulation, dosage and ideal route of administration to use progesterone.

The three main clinical strategies currently used to prevent preterm birth: progesterone, cervical cerclage and inserting a cerclage pessary, have not been sufficient to reduce the global rate of premature births, which has remained constant over the years. There is an urgent need for new therapeutic approaches that can offer solutions to this major public health problem.

The inventors of the present invention surprisingly have developed a new technology which join together the beneficial effects of progesterone and cerclage pessary to deliver in a single device the pharmacological effect of the hormone and the mechanical effect of the pessary for all gestation period from the moment pessary is installed, with the sole intervention of installing the device in the cervix.

This new device is a cerclage pessary made of dimethylsiloxane elastomer containing progesterone, which is inserted into the cervix of the patient at risk of preterm birth and remains installed without further intervention, except at the time of removal. The pessary releases progesterone continuously and sustainably throughout the time it is installed, which can be from 16 weeks of gestation until 36 6/7 weeks or until the time of delivery. Pessary does not need to be removed to be filled with progesterone to maintain progesterone levels delivered by the pessary through time, since progesterone content and its pattern of release are sufficient to provide hormone throughout the treatment period.

In the prior art does not exist a cervical pessary made of dimethylsiloxane elastomer containing progesterone with prolonged, sustained, and continuous release of the hormone, as described herein. Pessary design of the present invention ensures that local release of progesterone is maintained throughout the treatment period, without intervening the pessary to recharge or supplement the active ingredient.

In the prior art there are a diversity of vaginal devices locally delivering active ingredients, such as vaginal rings. As reference, patent documents U.S. Pat. No. 5,869,081, U.S. Pat. No. 415,991, US20080248017 disclose rings containing hormones, such as progesterone. Even though they are prolonged release rings, only release hormones for periods between 14-36 days.

US 20090264395 discloses a method which involves the use of an intravaginal ring or other devices of the prior art containing progesterone, and indicates that administration can be weekly or daily, to prevent preterm birth.

US20040089308 describes a cervical ring containing progesterone that create a suction engagement with the cervix to stay on the cervix. There is no mention to how long it releases progesterone.

Rings containing layers for releasing active ingredients, as in WO2012170578 and WO2006010097 are also describe. WO2011011099 describes a ring comprising at least three layers of a silicone elastomer.

Furthermore, in WO2009099586 are disclosed monolithic intravaginal rings comprising progesterone homogeneously dispersed in a polysiloxane elastomer and pharmaceutically acceptable hydrocarbon or glycerol esters of a fatty acid; process for their manufacture and use for treating a luteal phase defect in a patient. Progesterone is at a concentration of 15-30% by weight of the ring and is released for 1 to 14 days at a rate of approximately 15 to 25 mg/day. The ring is replaced after 7 days of its administration.

WO199922680 discloses a pessary including a surface receptacle; and an insertable medication cartridge that can be inserted into the receptacle. The device can easily be loaded into the pessary for use, and removed after a period of time, once the medication has been delivered from the cartridge. The device has sustained release over a period of 30-90 days.

There are several means to deliver active ingredients vaginally. Among these are vaginal rings which are used as vehicles or carriers for the active agent release at the local site. The purpose of these dispensers has only been local release without an additional effect of the device itself, for a limited period of time.

Moreover, the use of a pessary containing progesterone for preventing preterm birth has been suggested (Romero et al., 2013) and even DE20121009057 describes a rotational pessary with prolonged release of progesterone over an approximately 1-5 months period. This pessary containing the active ingredient in biodegradable layers, which are applied in the active sub-areas on the surface of the intrauterine device, so progesterone is carried out by one or more layers, depending on what stage of pregnancy the pessary is applied. According to the number of layers, the use of the active compound can be adapted for the time required of the active ingredient, and for example, a short application time will require one layer, and so on. Polymers are used as carriers of the application layer, mainly insoluble in water. Solvents or mixtures of selected solvents in which support material is incorporated are also used, for example, according to the quality of polymer solvent or miscibility with aqueous and oil phases. In solvent selection should also be considered miscibility of liquid carrier with body fluids, the external phase, and solidification of the carrier phase that can be influenced. The viscosity of the carrier phase can also be affected by characteristics of the solvent through the support, for example, molecular weight and concentration.

The active substance comprised in the pessary described in DE20121009057, is contained in at least one biodegradable layer, distributed over at least part of the surface of the support pessary, with a thickness of 0.01 to 2 mm, preferably 0.1-1 mm. It is also noted that the chamber located inside the support pessary, after the discharge of the active substance, can be refilled, or can be reload, preferably through an opening in the surface of the support pessary, wherein the amount of the active substance used is 10-100 mg, preferably 30-50 mg.

In the present invention, a pessary which is very different from pessary disclosed in DE20121009057 is described. The most substantial differences are: 1) pessary from DE20121009057 is formed by biodegradable layers containing progesterone; in contrast, the medicated pessary of the present invention does not have layers, but rather the hormone is distributed homogeneously throughout the body of the pessary. 2) The load of progesterone in DE20121009057 pessary is exhausted, thus the pessary has to be refilled with active ingredient; in contrast, the amount of progesterone in the pessary of the present invention is not exhausted, since the charge contained from manufacture, is sufficient and comfortably abundant for the whole period of treatment, which can be up to 5 or 6 months. 3) Formulations of pessaries are also very different; DE20121009057 pessary requires the addition of solvents; however, in this application, the solvent is the same structural polymer forming part of the ring and gives the necessary matrix for hormone prolonged release. 4) The design of DE20121009057 pessary is complex, since it has a chamber in which the active ingredient is loaded and a surface opening to refill said chamber; in contrast, the design of the present invention is simple, since it is a continuous body which does not require refilling, and surprisingly is suitable for hormone release for lengthy periods.

From all prior art, nothing would have predicted that the design of a cervical pessary made of dimethylsiloxane elastomer with a Room Temperature Vulcanizing (RTV) mechanism, such as the medicated pessary of the present invention could assure prolonged, sustained, and continuous release for a period as long as about 5-6 months from its installation. Nor was predictable that the hormone, in a pessary of significantly larger size than the devices containing progesterone disclosed in the prior art, such as for example vaginal rings, stayed homogeneously distributed and were released in sufficient amounts during the long period of treatment, ensuring at the same time the mechanical effect of a cerclage pessary.

DETAILED DESCRIPTION OF THE INVENTION

There is a need for an improved therapy to prevent preterm birth, which is safe, effective, easy to use, ensuring compliance and requiring minimal intervention on mother and fetus.

Medicated device of the present invention consists of a cerclage pessary formed with dimethylsiloxane elastomer containing homogeneously distributed progesterone, with prolonged release of the hormone for a long period of time of at least 5 to 6 months, and that is installed in women with risk of preterm birth, from the 16 weeks of gestation, without intervening again in the mother until the time of removal of the pessary at 36 6/7 weeks or upon childbirth. Progesterone diffuses through the polymer continuously, without altering the shape and integrity of the pessary, since the elastomer forming the polymeric matrix used in the present invention is not biodegradable. This ensures that the form of pessary remains intact until the end of treatment.

Does not exist in the prior art a cerclage pessary made of dimethylsiloxane elastomer with Room Temperature Vulcanizing (RTV), nor a pessary comprising progesterone cerclage homogeneously distributed throughout the body of the pessary, as described herein. This design of pessary surprisingly allowed inventors to add just enough progesterone and achieve sustained and prolonged release for as long as six months period.

Once the pessary is installed inside the mother, it should not be removed to be refilled with the active ingredient, because it is designed and formulated to contain the necessary amount of progesterone in the device for the entire treatment period and for prolonged and sustained release of the hormone, until the time it should be removed, at 36 6/7 weeks of gestation or later, or previously, if the treating physician deems it necessary.

MANUFACTURING PROCESS OF MEDICATED PESSARY

Figure 1:
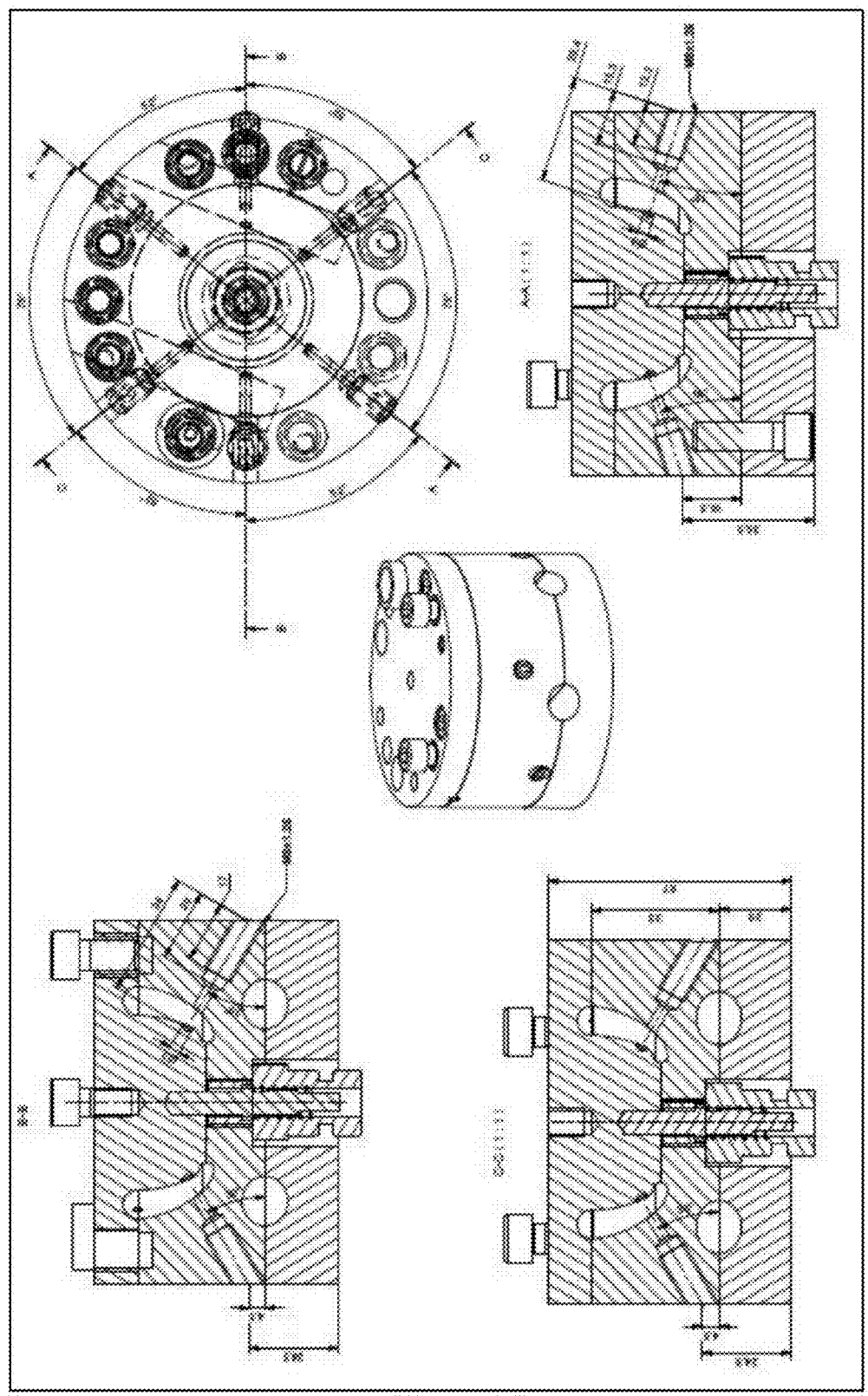
FIG. 1. Layout of the matrix designed and used for making the pessaries of this application. In cross sectional view can be seen location of the pins that perforate the pessary.
Figure 2:
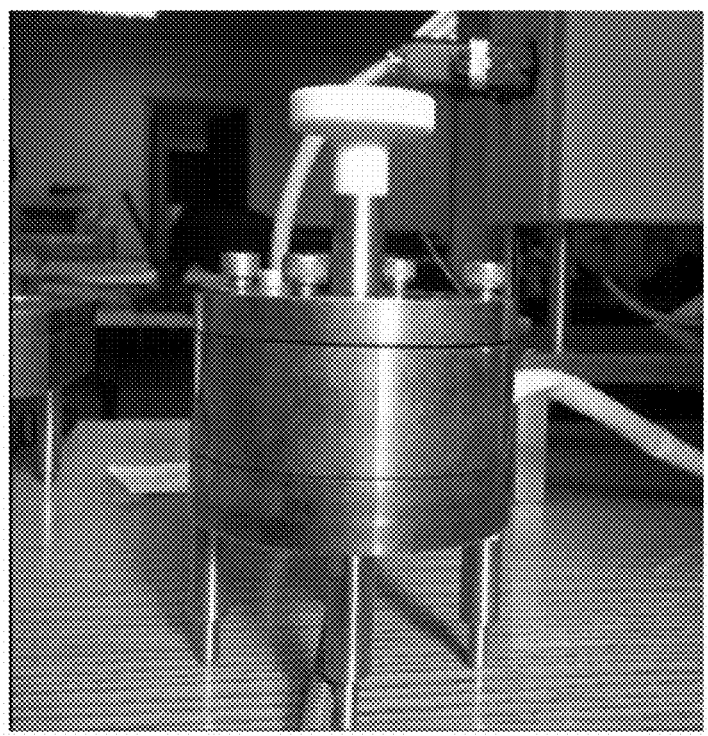
FIG. 2. Digital photograph of a bronze matrix used to produce the pessaries of the present invention, connected with the heating system.
Figure 3:
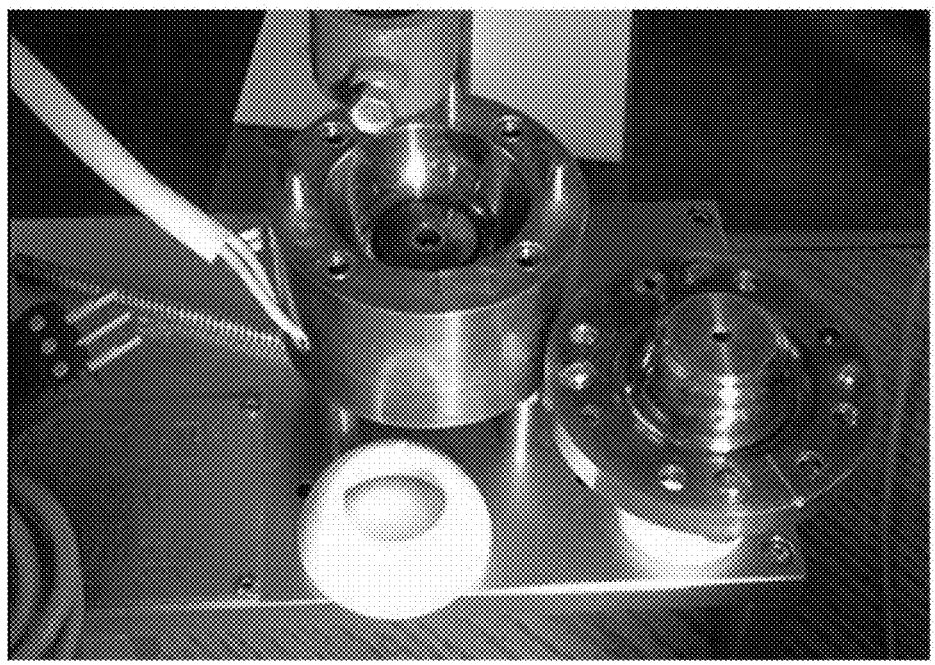
FIG. 3. Digital photograph of a bronze matrix used to produce the pessaries of the present invention, at rest, and a pessary obtained in this matrix.

For the manufacture of medicated pessary of the present invention, the design and construction of a matrix was performed by injection. The matrix was made from bronze SAE 640 material for the formation of medicated pessary according to specifications and layout shown in FIG. 1. The matrix has six perforation pins, a temperature control system, which contains heaters, thermocouple, board for electronic temperature control and a board base incorporated, as shown in FIGS. 2 and 3. To obtain the pessary, the blend of active ingredient with polymers is injected through a hole located on top of the matrix, filling indicator is located to one side at the upper end.

Steps of Manufacturing Process:
1. Weighing of Raw Materials
   In a pharmaceutical grade stainless steel vessel of suitable capacity the required amounts of each ingredient according to the formulations to be used as described in Table 1 are weighted. Transferred then to the mixer.
   Weighing of micronized progesterone in a polybag according to formulations to be tested as indicated in Table 1.
2. Mixing Procedure
   Slowly adding micronized progesterone to base polymer A with manual stirring, avoiding adding air; date of incorporation of the micronized progesterone to polymer must be recorded. Performing quality control to assess blend uniformity.
3. Polymerization Process
   Extracting, weighing and transferring an aliquot of the blend obtained in section 2 to a stainless steel vessel, according to the ratio of polymer A and B to be used, as indicated for each formulation in Table 1.
   Mixing immediately after polymer addition until the mixture is homogeneous (uniform and brilliant appearance), recording date and time of the preparation for each aliquot in a timesheet.
   Filling the stainless steel injector of suitable capacity with this final blend, and introducing to the mold inlet hole.
   Keeping the blend injected into the cast for 15-20 minutes at a temperature of 80±10° C., recording time and temperature in the timesheet.
   Once the process has been completed, open the matrix and remove the pessary.

Physical Characteristics of Progesterone Cerclage Pessary of the Present Invention Cerclage pessary of the present invention is made with dimethylsiloxane elastomer with RTV reaction mechanism.

Figure 4:
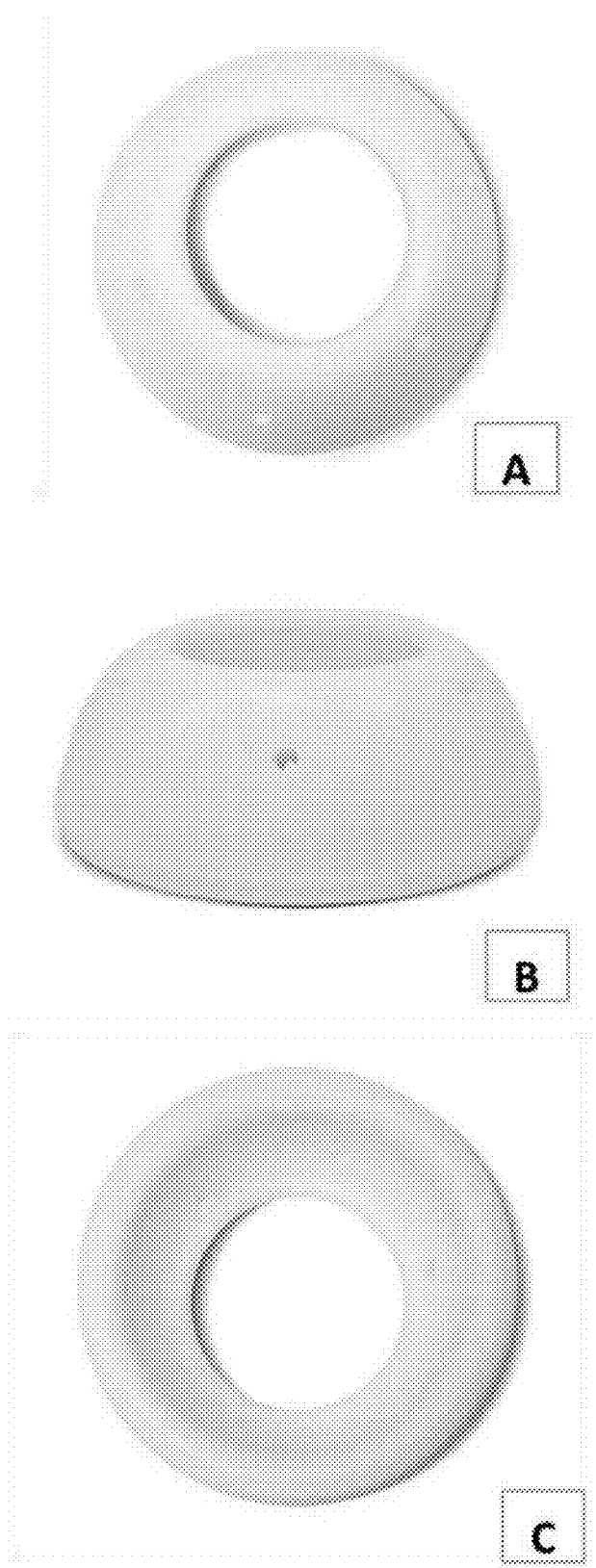
FIG. 4. Digital photographs of a pessary of the present invention Table A: View from the top end, which is installed in the cervix towards the uterus Table B: Side view which shows the holes in the curved surface of the pessary Table C: View from the lower end of the pessary, where their rounded ends can be seen.

It is a white, flexible, conically circular device, with a firm consistency, with a centered hole and six holes distributed on its surface, as shown in FIG. 4.

It have been reported the occurrence of an increased vaginal discharge with the use of pessaries and vaginal rings, so in the present invention, to facilitate drainage, a pessary having holes distributed throughout the section is preferably used. The holes have a diameter of 3.0 mm±0.2 mm.

Figure 5:
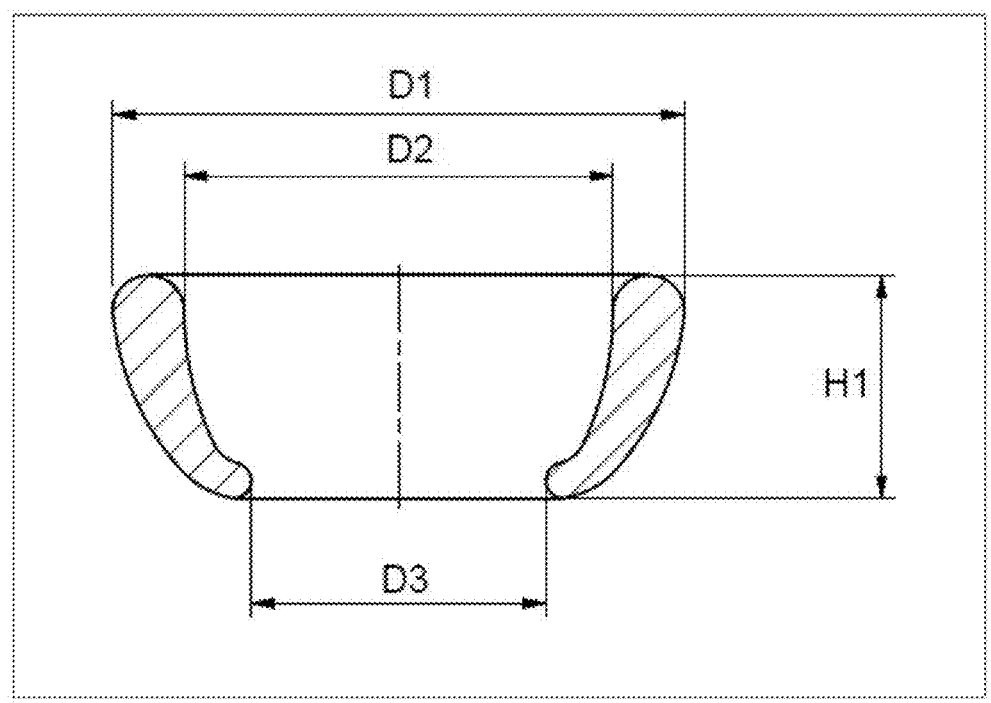
FIG. 5. Layout of the medicated cerclage pessary of the present invention. The locations of the main dimensions of the pessary are indicated. D1: Larger outer diameter; D2: Larger Inner Diameter; D3: Smaller diameter; H1: Height.

In the scheme shown in FIG. 5, the locations of the following dimensions for the pessary of the present invention are shown:

Larger outer diameter (D1): 65 mm±5 mm
Larger Inner Diameter (D2): 50 mm±5
Height (H1): 25 mm±2 mm
Smaller diameter (D3): 33.5 mm±1.5 mm
Weight of the medicated pessary is 30 g±5 g.

Exemplary Formulations

Cerclage pessaries comprising different amounts of progesterone, homogeneously distributed throughout the body of the device, in quantities from 20% to 30% w/w were made. These formulations comprise different proportions of RTV silicone elastomer.

In Table 1 General Formulations (GF) of the present invention are described. Different ratios of polymers used are specified.

TABLE 1

Formulations of cerclage pessaries containing progesterone with different ratios between Polymer A and Polymer B. Each formulation was expressed as General Formula (GF) in % w/w.

| Ingredient | % v/v | | | | | | | | |
|---|---|---|---|---|---|---|---|---|---|
| | GF-1 | GF-2 | GF-3 | GF-4 | GF-5 | GF-6 | GF-7 | GF-8 | GF-9 |
| Micronized progesterone | 20.0-30.0 | 20.0-30.0 | 20.0-30.0 | 20.0-30.0 | 20.0-30.0 | 20.0-30.0 | 20.0-30.0 | 20.0-30.0 | 20.0-30.0 |
| Polymer A: polydimethylsiloxane-vinyl polymer + amorphous silica (25%) + platinum catalyst | 58.33-66.67 | 60.0-68.57 | 61.25-70.0 | 62.22-71.11 | 63.0-72.0 | 63.64-72.73 | 64.17-73.33 | 64.62-73.85 | 65.0-74.29 |
| Polymer B: Copolymer of Dimethyl methylhydrogen siloxane (20%) + polydimethylsiloxane | 11.67-13.33 | 10.0-11.43 | 8.75-10.0 | 7.78-8.89 | 7.0-8.0 | 6.36-7.27 | 5.83-6.67 | 5.38-6.15 | 5.0-5.71 |
| Total content | 100 | 100 | 100 | 100 | 100 | 100 | 100 | 100 | 100 |
| (Polymer A:Polymer B) ratio | 5:1 | 7:1 | 8:1 | 9:1 | 10:1 | 11:1 | 12:1 | 13:1 | 14:1 |

Specific Formulations of Medicated Cervical Pessary:

Pessaries containing 20 to 30% of progesterone formed by dimethylsiloxane polymers, containing a variable ratio of Polymer A and Polymer B were made, wherein the first one is polydimethylsiloxane-vinyl polymer with 25% amorphous silica and a platinum catalyst, and the second one is a copolymer of 20% dimethyl methylhydrogen siloxane with polydimethylsiloxane.

In following Tables 2 to 6 pessary formulations of the present invention are shown. All comprising the same elastomer but formed with different proportions of the starting polymers.

TABLE 2

Formulations of pessary medicated with progesterone in Polymer A:Polymer B = 6:1 and 7:1 ratios

| Ingredient | Ratio A:B = 6:1 % W/W | | | | | Ratio A:B = 7:1 % W/W | | | | |
| --- | --- | --- | --- | --- | --- | --- | --- | --- | --- | --- |
| Micronized progesterone | 20 | 22.5 | 25 | 28 | 30 | 20 | 22.5 | 25 | 28 | 30 |
| Polymer A: polydimethylsiloxane-vinyl polymer + amorphous silica (25%) + platinum catalyst | 66.67 | 64.58 | 62.50 | 60.00 | 58.33 | 68.57 | 66.43 | 64.29 | 61.71 | 60.00 |
| Polymer B: Copolymer of Dimethyl methylhydrogen siloxane (20%) + polydimethylsiloxane | 13.33 | 12.92 | 12.50 | 12.00 | 11.67 | 11.43 | 11.07 | 10.71 | 10.29 | 10.00 |
| Total content | 100 | 100 | 100 | 100 | 100 | 100 | 100 | 100 | 100 | 100 |

TABLE 3

Formulations of pessary medicated with progesterone in a Polymer A:Polymer B = 8:1 and 9:1 ratios

| Ingredient | Ratio A:B = 8:1 % W/W | | | | | Ratio A:B = 9:1 % W/W | | | | |
| --- | --- | --- | --- | --- | --- | --- | --- | --- | --- | --- |
| Micronized progesterone | 20 | 22.5 | 25 | 28 | 30 | 20 | 22.5 | 25 | 28 | 30 |
| Polymer A: polydimethylsiloxane-vinyl polymer + amorphous silica (25%) + platinum catalyst | 70.00 | 67.81 | 65.63 | 63.00 | 61.25 | 71.11 | 68.89 | 66.67 | 64.00 | 62.22 |
| Polymer B: Copolymer of Dimethyl methylhydrogen siloxane (20%) + polydimethylsiloxane | 10.00 | 9.69 | 9.38 | 9.00 | 8.75 | 8.89 | 8.61 | 8.33 | 8.00 | 7.78 |
| Total content | 100 | 100 | 100 | 100 | 100 | 100 | 100 | 100 | 100 | 100 |

TABLE 4

Formulations of pessary medicated with progesterone in Polymer A:Polymer B = 10:1 and 11:1 ratios

| Ingredient | Ratio A:B = 10.1:1 % W/W | | | | | Ratio A:B = 11:1 % W/W | | | | |
| --- | --- | --- | --- | --- | --- | --- | --- | --- | --- | --- |
| Micronized progesterone | 20 | 22.5 | 25 | 28 | 30 | 20 | 22.5 | 25 | 28 | 30 |
| Polymer A: polydimethylsiloxane- | 72.00 | 69.75 | 67.50 | 64.80 | 63.00 | 72.73 | 70.45 | 68.18 | 65.45 | 63.64 |

TABLE 4-continued

Formulations of pessary medicated with progesterone in Polymer A:Polymer B = 10:1 and 11:1 ratios

| Ingredient | Ratio A:B = 10.1:1 % W/W | | | | | Ratio A:B = 11:1 % W/W | | | | |
|---|---|---|---|---|---|---|---|---|---|---|
| vinyl polymer + amorphous silica (25%) + platinum catalyst | | | | | | | | | | |
| Polymer B: | 8.00 | 7.75 | 7.50 | 7.20 | 7.00 | 7.27 | 7.05 | 6.82 | 6.55 | 6.36 |
| Copolymer of Dimethyl methylhydrogen siloxane (20%) + polydimethylsiloxane | | | | | | | | | | |
| Total content | 100 | 100 | 100 | 100 | 100 | 100 | 100 | 100 | 100 | 100 |

TABLE 5

Formulations of pessary medicated with progesterone in Polymer A:Polymer B = 12:1 and 13:1 ratios

| Ingredient | Ratio A:B = 12:1 % W/W | | | | | Ratio A:B = 13:1 % W/W | | | | |
|---|---|---|---|---|---|---|---|---|---|---|
| Micronized progesterone | 20 | 22.5 | 25 | 28 | 30 | 20 | 22.5 | 25 | 28 | 30 |
| Polymer A: polydimethylsiloxane-vinyl polymer + amorphous silica (25%) + platinum catalyst | 73.33 | 71.04 | 68.75 | 66.00 | 64.17 | 73.85 | 71.54 | 69.23 | 66.46 | 64.62 |
| Polymer B: | 6.67 | 6.46 | 6.25 | 6.00 | 5.86 | 6.15 | 5.96 | 5.77 | 5.54 | 5.38 |
| Copolymer of Dimethyl methylhydrogen siloxane (20%) + polydimethylsiloxane | | | | | | | | | | |
| Total content | 100 | 100 | 100 | 100 | 100 | 100 | 100 | 100 | 100 | 100 |

TABLE 6

Formulations of pessary medicated with progesterone in Polymer A:Polymer B = 14:1 ratio

| Ingredient | Ratio A:B = 14:1 % W/W | | | | |
|---|---|---|---|---|---|
| Micronized progesterone | 20 | 22.5 | 25 | 28 | 30 |
| Polymer A: polydimethylsiloxane-vinyl polymer + amorphous silica (25%) + platinum catalyst | 74.29 | 71.96 | 69.64 | 66.86 | 65.00 |
| Polymer B: | 5.71 | 5.54 | 5.36 | 5.14 | 5.00 |
| Copolymer of Dimethyl methylhydrogen siloxane (20%) + polydimethylsiloxane | | | | | |
| Total content | 100 | 100 | 100 | 100 | 100 |

Cervical pessaries were prepared containing 5 g to 10.5 g of progesterone, with ratios of polymer A to B as shown in Tables 1 to 6.

Identity and assessment of active principle in the medicated pessary of the present invention:

To determine the identity and assessment of progesterone contained in pessaries, the following conditions and procedures were used:

Chromatographic Conditions:
Column: Agilent Eclipse XDB C-18 (4.6×150 mm) (5 μM)
Mobile phase: acetonitrile: 60%
Water: 40%
Flow rate: 1.0 mL/min
Wavelength: 240 nm
Injection volume: 50 μL
Approximate Retention time: 8.0 min
Standard Solution:

Weighing accurately about 50 mg±1 mg progesterone secondary standard in a volumetric flask of 100 mL. Adding 60 mL of methanol, sonicating 2 minutes, diluting to volume with methanol. Taking an aliquot of 2.0 mL and transferring to a 100 mL flask with mobile phase. Homogenizing. Filtering through a membrane filter of 0.45 μm (C=0.01 mg/mL).

Sample Solution:

Weighing 10 pessaries and determining their average weight: Taking a pessary and make a cut to open it. Carefully longitudinally cutting into pieces of about 2 mm and put the pieces in a clean dry vessel. Weighing the equivalent of a pessary and bringing to a 250 mL Erlenmeyer flask with tight-fitting lid, adding 150 mL of dichloroethane, covering, placing on a magnetic stirrer and stirring for 18 hours.

Quantitatively transferring the extract obtained to a 200 mL volumetric flask rinsing the pessary residue with small amounts of dichloroethane, bringing to volume with dichloroethane, homogenizing.

Taking a 2.0 mL aliquot of this solution and transferring to a 200 mL beaker, carefully evaporating to dryness under nitrogen stream, dissolving the residue with 25 mL of methanol, gently sonicating 2 minutes and quantitatively transferring to a 50 ml volumetric flask rinsing with small amounts of methanol, bringing to volume with methanol, homogenizing. From this solution taking an aliquot of 5.0 mL volumetric and bringing to a 100 mL volumetric flask with mobile phase. Homogenizing. Filtering through a membrane filter of 0.45 μm (C=0.01 mg/mL).
Adjusting Dilutions for the Pessary, as Needed
Procedure:

Separately injecting 50 mL of standard and sample solutions, obtaining the corresponding chromatograms and determining the area under the peak.
Calculations:

$$g/pessary = \frac{As}{Ast} \times \frac{Wst}{100} \times \frac{2}{100} \times \frac{\%R}{100} \times \frac{200}{Wspl} \times \frac{50}{2} \times \frac{100}{5} \times \frac{1}{1000} \times PAW$$

$$\%VD = g/pessary \times 100$$

Wherein:
As=Average area under the peak of progesterone in the sample solution
Ast=Average area under the peak of progesterone in the standard solution
Wst=Weight of standard of progesterone, mg
% R=Purity of Standard, in %
Wspl=Weight of sample in mg
PAW=Pessary average weight in mg.

Using the implemented and validated analytical method, the above tests were subjected to physical-chemical analysis, complying with the established product specifications based on design requirements.
Studies of In Vitro Release It was developed an experimental protocol for the study of in vitro hormonal release for a period of at least five months in order to evaluate the release profile, quantifying mg of released progesterone per day within the indicated period of time.
Methodology:
Method: UV spectrophotometry
Wavelength: 262.4 nm (Diffusion Medium)
240 nm (Samples)
Quartz cuvettes: 1 cm depth
Diffusion Medium:

Adding about 64.26 mL of 50% benzalkonium chloride in a precipitate vessel, adding about 200 mL of double distilled water, dissolving until is completely dissolved. Transfer quantitatively the benzalkonium chloride solution to a 1.0 L flask and dilute to volume with bidistilled water. The resulting solution is then transferred to a polyethylene drum with a tap containing 23 L of double-distilled water inside, stirring until homogenization. The concentration obtained is 1:750.

Measuring the absorbance of the diffusion medium at 262.4 nm in cells of 1 cm using distilled water as a blank. The absorbance must range from 1.3 to 1.6, otherwise the solution should be discarded.

Stock of Standard Solution:

Weighing accurately about 25 mg of standard progesterone, transferring to a 50 mL volumetric flask, adding 25 mL of ethanol, dissolving and bringing to volume with ethanol. Dividing into 5 mL tubes with screw cap, labeling with a name, concentration and date. Keeping refrigerated.
Diluted Standard Solution:

From the stock of standard solution, previously heated to room temperature, an aliquot of 200 μL is taken and transferred to a 10 mL volumetric flask and brought to volume with diffusion medium (C=0.01 mg/mL). Repeating the procedure four times.
Sample Solutions:

Adding 900 mL of diffusion medium to six 1000 mL polyethylene wide-mouth screw top bottles. Individually weighing 6 pessaries, recording their weight and assigning a number to each one of them. Tying each pessary with a suitable length polyethylene yarn to completely immerse in diffusion medium, introducing the pessaries into the bottles and then fixing the yarn on the outer surface thereof with tape.

Pessaries must be positioned at 2±0.2 cm from the base of the bottle.

Labeling each bottle with the weight and number of the corresponding pessary. Covering each bottle, and placing them in a suitable water bath at 37±0.5° C. and stirring at 100 rpm±5 rpm.

Checking and recording temperature and stirring speed of the bathroom daily.

Every 24 hours, at the same time, changing diffusion medium of each bottle. Taking an aliquot of 20 mL of each bottle and discarding the rest of the diffusion medium on weekdays. Taking an aliquot of 10 mL and transferring to a 50 mL volumetric flask, bringing to volume with diffusion medium from the same batch. Absorbance readings of 0.3 to 0.7 must be obtained or otherwise it must be adjusted with diffusion medium of the same batch, as needed.

Measuring absorbance of aliquots and diluted standard solutions in 1 cm quartz cells at 240 nm and using diffusion medium as a blank.

Carrying on the test in the same manner until completion of 150 days.

When calculating the average absorbance of diluted standard solutions, the coefficient of variation should not exceed 2.0%. If this requirement is not met, dilutions must be repeated. Calculating mg progesterone released per day, according to the following formula:

mg of Progesterone=Absorbance Factor×As

Wherein:
As=Absorbance of the sample $$\text{Absorbance Factor} = \frac{Cds \times Vt \times Vds}{AAs \times Vs}$$

wherein:
Cds: Concentration of diluted standard solution.
Vt: total volume of diffusion medium 900 mL
Vds: Final Dilution Volume of sample.
AAs: Average Absorbance of diluted standard solution.
Vs: volume of the sample taken for dilution.

In vitro release studies were performed with medicated pessaries described in Tables 2-6, using the described analytical procedure.

Figure 6:
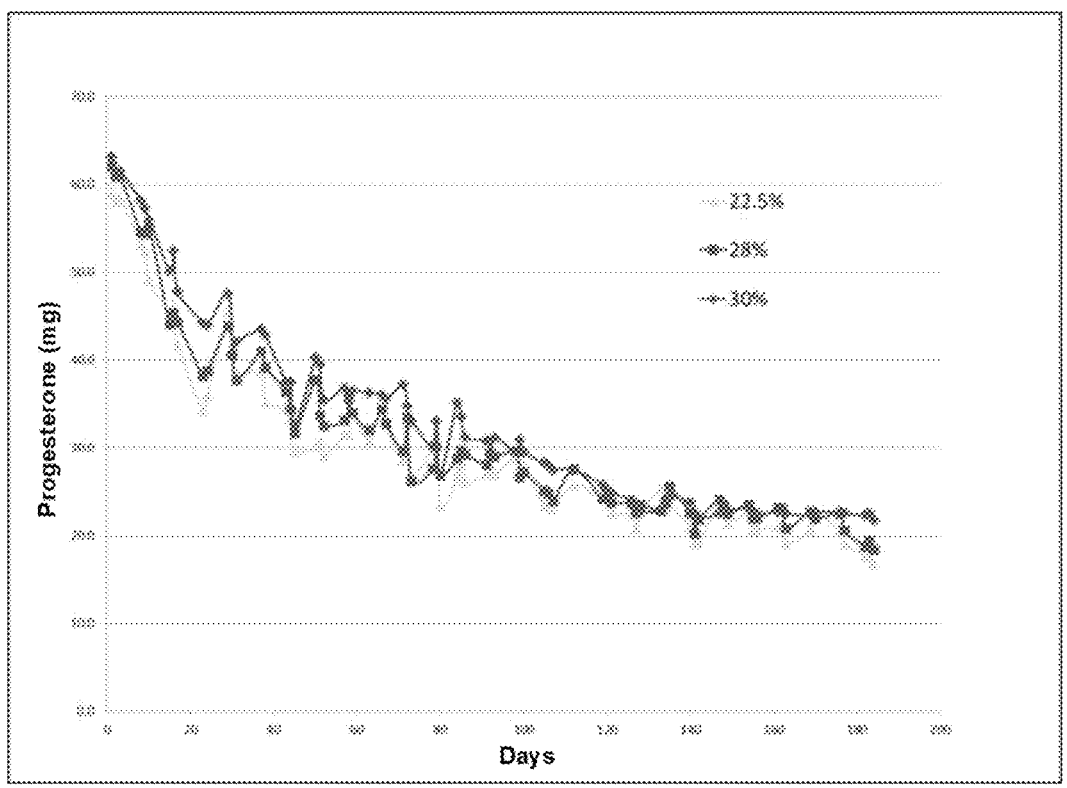
FIG. 6. In vitro release profile of progesterone from cerclage pessaries comprising 22.5%, 28% and 30% of progesterone. Pessaries comprise Polymer A and B in a ratio 8:1 (R=8:1).

In FIG. 6 it is observed progesterone release from three pessaries prepared with a polymer ratio of A:B=8:1 (R=8:1)

containing different amounts of progesterone, 22.5%, 28% and 30%, corresponding to 6.75 g, 8.4 g and 9 g of progesterone in each pessary, respectively. Even though the release of progesterone from 22.5% pessaries tends to be low, no significant differences between the three curves are observed. Initial release (day 1) was 59, 62.1 and 63.1 mg, respectively, reaching 21.4, 22.4 and 23 mg on day 150 (5 months progesterone release), and 17, 9, 18.8 and 22.3 mg on day 182 (6 months progesterone release). The average amount of progesterone released between 120 to 150 days was 22.4, 18.8 and 22.3 mg, respectively.

These results revealed no significant differences in progesterone release from pessaries containing 22.5% 28% and 30% of hormone, probably this is due to the fact that saturation was reached in both pessary loading and active ingredient release.

Additionally, the effect of different ratios of polymer A and B on the hormone release profile was evaluated due to the complexity in the process of the curing of polymers, and the difficulty in polymerization that can occur when the ratios are inadequate.

Figure 7:
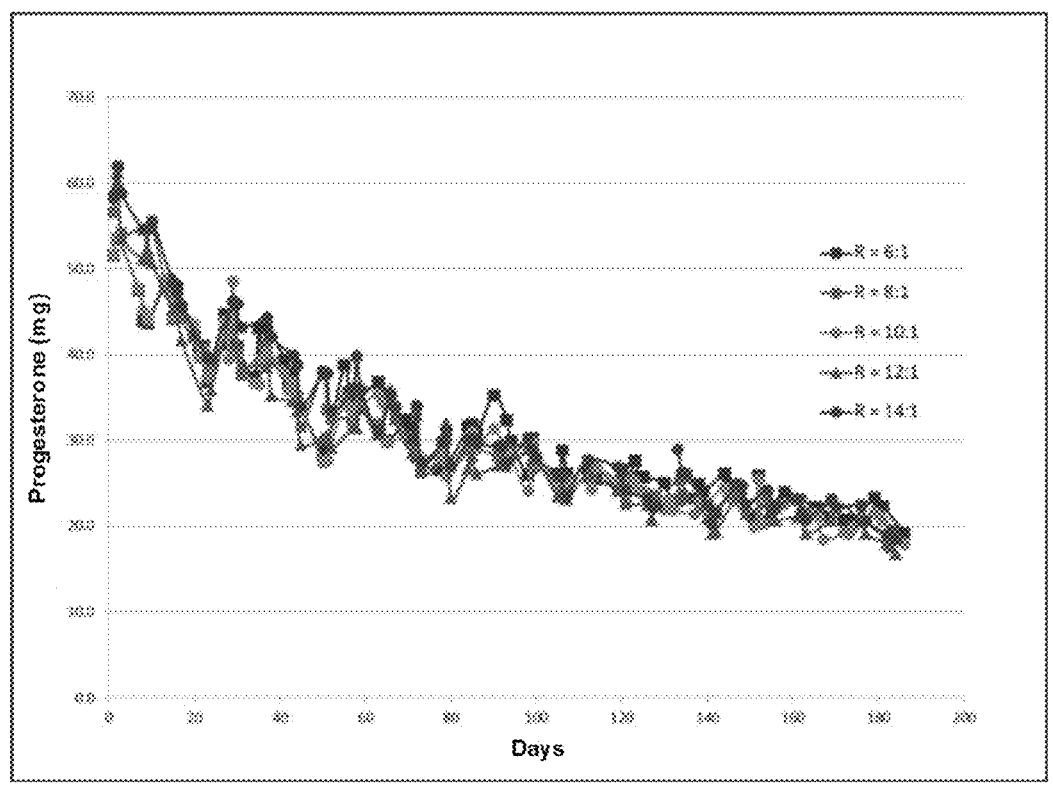
FIG. 7. In vitro release profile of progesterone from cerclage pessaries comprising 22.5% of progesterone. Pessaries comprise Polymer A and B in a ratio (R) of 6:1, 8:1, 10:1, 12:1 and 14:1.

FIG. 7 shows release from pessaries containing 22.5% of progesterone in polymer ratios (R) of 6:1, 8:1, 10:1, 12:1 and 14:1. The result was surprising, since the release profile is virtually the same and no differences were observed in both initial release (day 1) and the amount of progesterone released in last months (120-150 days) reaching 24.6, 23.3, 23.0, 22.4 and 23.9 mg, respectively.

Thus, the preferred ratios of the present invention are from 6:1 to 14:1 for polymer A relative to polymer B, since it did not significantly affected the amount of progesterone released in the beginning and in last months, as well as it did not modify the hormone release profile from pessaries.

Clinical Studies in Women with Risk of Preterm Birth
Clinical Case 1:

A 26 year old woman with a history of preterm vaginal birth in 2011.

In the current pregnancy she was in control at a High Risk Obstetric Clinic because she had a dichorionic diamniotic twin pregnancy with morphologically normal fetuses. In a pregnancy control at 18 weeks a transvaginal ultrasound to measure cervical length was performed, which results in 35 mm (under 25 percentile for said gestational age). She was hospitalized at 20 weeks and 1 day, because a cervical shortening to 28 mm is detected in the last 2 weeks. Unable to provide some measure for effective prevention of preterm birth, it is proposed to the patient using a pessary medicated with progesterone of the present invention. She willingly agreed to the installation thereof, which is performed without difficulty after signing the informed consent. The pessary was installed when she was 21 weeks 4 days of gestation. Cervical length was 30 mm after pessary installation maintaining at that length in the following controls. In her later controls she did not referred discomforts such as increased vaginal discharge or constipation. She again was hospitalized when she was 32 weeks of gestation for having sensitive uterine contractions. At that time a new cervical length measurement is performed resulting in a 23 mm length with a well positioned pessary. Since the event does not progress to preterm birth, she is discharged at 32 weeks and 4 days.

She again assisted to a medical consultation at 34 weeks and 2 days referring having expelled the pessary the prior night (34 weeks and 1 day). The case is clinically re-evaluated and for exceeding the 34 weeks of gestation is decided not to reinstall the pessary, indicating partial rest.

The patient has her childbirth through an elective cesarean section at 37 weeks and one day. The newborn boys of 2,200 and 2,780 grams were born in good conditions and are discharged on the eighth day of life with his mother.

Clinical Case 2:

A 38 year old multigesta woman with a past history of three previous miscarriages and no delivery.

In a private practice consultation for control of singleton pregnancy, a cervical length of 38 mm at 12 weeks of gestation is detected. In a subsequent control at 24 weeks and 4 days a cervical length of 10 mm with cervical wedge or funnel is found. She is hospitalized for deciding management alternatives. After five days of rest, a new transvaginal ultrasound results in a 20 mm neck. The patient is proposed to use a pessary medicated with progesterone, to which she willingly agreed. After signing the informed consent, the pessary was installed at 25 weeks and 4 days, without difficulty or discomfort for the patient. She is controlled periodically and the patient did not refer discomfort with the pessary (no increased vaginal discharge or constipation). In a control when she was 29 weeks and 4 days, a cervical length of 15.8 mm with a well positioned pessary is found. The patient is clinically and sonographically controlled monthly, no more cervical shortening or discomfort attributable to the use of the pessary is detected. Pessary is removed at 36 weeks and the patient had a spontaneous vaginal delivery at 38 weeks of gestation.

Transvaginal Ultrasound and Magnetic Resonance Imaging

Figure 8:
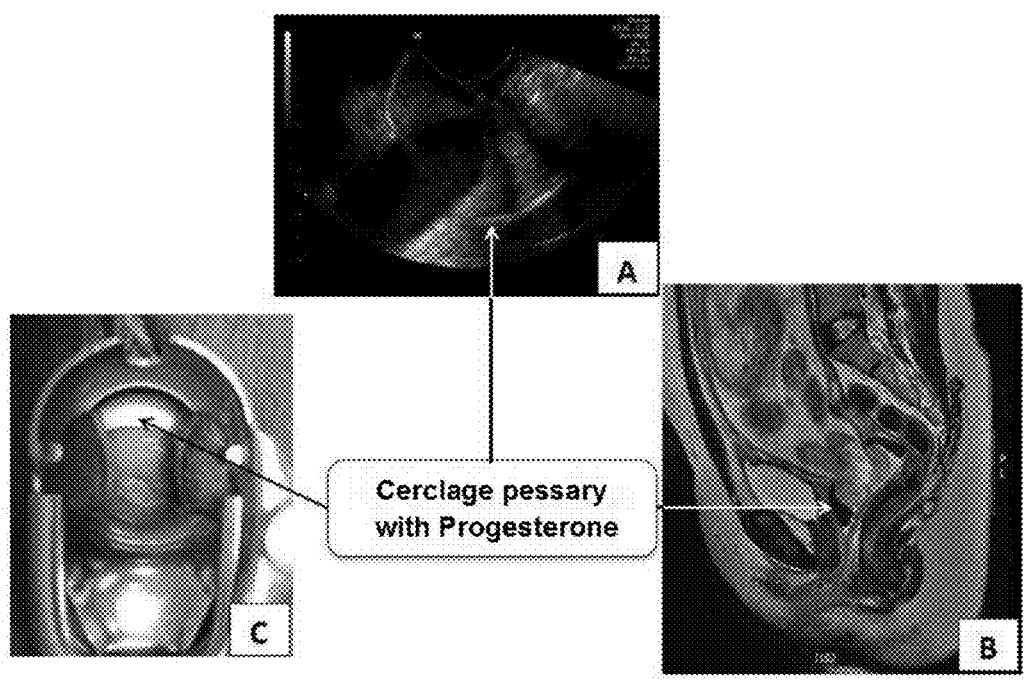
FIG. 8. Images of Transvaginal Ultrasound (EcoTV), Nuclear Magnetic Resonance (NMR) and Digital Photography Table A: EcoTV in a woman at risk of preterm birth, which has the pessary of the present invention installed surrounding the cervix Table B: NMR image of the same woman, wherein the pessary containing and affirming the cervix is displayed Table C. Digital photography of the woman having a short cervix, with the pessary of the present invention located in the cervix.

The patient of the clinical case 2 was subjected to a Transvaginal ultrasound (Eco TV) and Nuclear Magnetic Resonance (NMR) to measure and evaluate cervical length, and placement and positioning of medicated pessary of the present invention. As shown in FIG. 8, the Eco TV (Table A) shows the position of the pessary in the cervix and NMR (Table B) clearly shows how the pessary with progesterone of the present invention surrounds the cervix supporting and protecting it from uterus weight. In the digital photography (Table C) the pessary of the present invention installed in the patient is seen and the neck within the pessary is observed. Although this patient initially had a fairly short neck (10 mm), the pessary was very well positioned.

REFERENCES

Alfirevic Z, Owen J, Carreras Moratonas E, Sharp A N, Szychowski J M, Goya M. Vaginal progesterone, cerclage or cervical pessary for preventing preterm birth in asymptomatic singleton pregnant women with a history of preterm birth and a sonographic short cervix. Ultrasound Obstet Gynecol. 2013; 41(2):146-51.

Arabin B, Alfirevic Z. Cervical pessaries for prevention of spontaneous preterm birth: past, present and future. Ultrasound Obstet Gynecol 2013; 42: 390-399.

Arabin B, Halbesma J R, Vork F, Hübener M, van Eyck J. Is treatment with vaginal pessaries an option in patients a sonographically detected short cervix? J Perinat Med 2003; 31: 122-33.

Arabin B, Roos C, Kollen B, Van Eyck J. Comparison of transvaginal sonography in recumbent and standing maternal positions to predict spontaneous preterm birth in singleton and twin pregnancies. Ultrasound Obstet Gynecol 2006; 27: 377-386.

Astle S, Slater D M, Thornton S. The involvement of progesterone in the onset of human labour. Eur J Obstet Gynecol Reprod Biol 2003; 108: 177-81.

Berghella V, Bega G, Tolosa J E, Berghella M. Ultrasound assessment of the cervix. Clin Obstet Gynecol 2003; 46(4): 947-962.

Berghella V. Novel developments on cervical length tamizaje and progesterone for preventing preterm birth. BJOG 2009; 116: 182-187.

Campbell S. Universal cervical-length screening and vaginal progesterone prevents early preterm births, reduces neonatal morbidity and is cost saving: doing nothing is no longer an option. Ultrasound Obstet Gynecol. 2011; 38:1-9.

Cannie M M, Dobrescu O, Gucciardo L, Strizek B, Ziane S, Sakkas E, Schoonjans F, Divano L, Jani J C. Arabin cervical pessary in women at high risk of preterm birth: a magnetic resonance imaging observational follow-up study. Ultrasound Obstet Gynecol 2013; 42(4): 426-433.

Caritis S N, Simhan H. Cervical pessary use and preterm birth: how little we know. Lancet 2012; 379(9828): 1769-70.

Celik E, To M, Gajewska K, Smith G C S, Nicolaides K H, and the Fetal Medicine Foundation Second Trimester Screening Group. Cervical length and obstetric history predict spontaneous preterm birth: development and validation of a model to provide individualized risk assessment. Ultrasound Obstet Gynecol 2008; 31: 549-54.

Conde-Agudelo A, Romero R, Nicolaides K H, Chaiworapongsa T, O'Brien J, Cetingoz E, Da Fonseca E, Creasy G, Soma-Pillay P, Fusey S, Cam C, Alfirevic Z, Hassan S. Vaginal progesterone versus cervical cerclage for the prevention of preterm birth in women with a sonographic short cervix, singleton gestation, and previous preterm birth: a systematic review and indirect comparison meta-analysis. Am J Obstet Gynecol 2013; 208 (1):42.e1-42.e18.

Cross R G. Treatment of habitual abortion due to cervical incompetence. Lancet 1959; 2: 127.

Da Fonseca E B, Celik E, Parra M, Singh M, Nicolaides K H. Progesterone and the risk of preterm birth among women with a short cervix. N Engl J Med 2007; 357: 462-469.

DeFranco E A, O'Brien J M, Adair C D, Lewis D F, Hall D R, Fusey S, Soma-Pillay P, Porter K, How H, Schakis R, Eller D, Trivedi Y, Vanburen G, Khandelwal M, Trofatter K, Vidyadhari D, Vijayaraghavan J, Weeks J, Dattel B, Newton E, Chazotte C, Valenzuela G, Calda P, Bsharat M, Creasy G W. Vaginal progesterone is associated with a decrease in risk for early preterm birth and improved neonatal outcome in women with a short cervix: a secondary analysis from a randomized, double-blind, placebo-controlled trial. Ultrasound Obstet Gynecol 2007; 30: 697-705.

Dodd J M, Crowther C A, Cincotta R, Flenady V and Robinson J S. Progesterone supplementation for preventing preterm birth: a systematic review and meta-analysis. Acta Obstet Gynecol Scand 2005; 84: 526-533.

Draper E S, Manktelow B, Field D J, James D. Prediction of survival for preterm births by weight and gestational age: retrospective population based study. BMJ 1999; 319: 1093-1097.

Goldenberg R L, Culhane J F, Iams J, Romero R. The epidemiology and etiology of preterm birth. Lancet 2008; 371: 75-84.

Goldenberg R L, Iams J D, Miodovnik M, Van Dorsten J P, Thurnau G, Bottoms S, Mercer B M, Meis P J, Moawad A H, Das A, Caritis S N, McNellis D. The preterm prediction study: risk factors in twin gestations. National Institute of Child Health and Human Development Maternal-Fetal Medicine Units Network. Am J Obstet Gynecol 1996; 175: 1047-1053.

Goya M, Pratcorona L, Merced C, Rodó C, Valle L, Romero A, Juan M, Rodriguez A, Muñoz B, Santacruz B, Bello-Muñoz J C, Llurba E, Higueras T, Cabero L, Carreras E; Pesario Cervical para Evitar Prematuridad (PECEP) Trial Group. Cervical pessary in pregnant women with a short cervix (PECEP): an open-label randomised controlled trial. Lancet 2012; 379(9828): 1800-1806.

Grazzini E, Guillon G, Mouillac B, Zingg H H. Inhibition of oxytocin receptor function by direct binding of progesterone. Nature 1998; 392(6675):509-12.

Hassan S S, Romero R, Vidyadhari D, Fusey S, Baxter J K, Khandelwal M, Vijayaraghavan J, Trivedi Y, Soma-Pillay P, Sambarey P, Dayal A, Potapov V, O'Brien J, Astakhov V, Yuzko O, Kinzler W, Dattel B, Sehdev H, Mazheika L, Manchulenko D, Gervasi M T, Sullivan L, Conde-Agudelo A, Phillips J A, Creasy G W. Vaginal progesterone reduces the rate of preterm birth in women with a sonographic short cervix: a multicenter, randomized, double-blind, placebo-controlled trial. Ultrasound Obstet Gynecol 2011; 38(1): 18-31.

Heath V C, Southall T R, Souka A P, Elisseou A, Nicolaides K H. Cervical length at 23 weeks of gestation: prediction of spontaneous preterm delivery. Ultrasound Obstet Gynecol 1998; 12: 312-317.

Iams J D, Goldenberg R L, Meis P J, y cols, and the National Institute of Child Health and Human Development Maternal Fetal Medicine Unit Network. The length of the cervix and the risk of spontaneous premature delivery. N Engl J Med 1996; 334: 567-72.

Iams J D, Romero R, Culhane J F, Goldenberg R L. Primary, secondary, and tertiary interventions to reduces the morbidity and mortality of preterm birth. Lancet 2008; 371: 164-175.

Jayasooriya, G S and Lamont, R F. The use of progesterone and other progestational agents to prevent spontaneous preterm labour and preterm birth. Expert Opin. Pharmacother. 2009, 10(6): 1007-1016.

Marlow N, Wolke D, Bracewell M A, Samara M. Neurologic and developmental disability at six years of age after extremely preterm birth. N Engl J Med 2005; 352: 9-19.

Martin J A, Hamilton B E, Sutton P D, Ventura S J, Menacher F, Munson M L. Births: final data for 2002. Natl Vital Stat Rep 2003; 52: 1-113.

Menon R. Spontaneous preterm birth, a clinical dilemma: etiologic, pathophysiologic and genetic heterogeneities and racial disparity. Acta Obstet Gynecol Scand. 2008; 87(6): 590-600.

Owen J, Yost N, Berghella V, Thom E, Swain M, Dildy G A, III, Miodovnik M, Langer O, Sibai B, McNellis D. Mid-trimester endovaginal sonography in women at high risk for spontaneous preterm birth. JAMA 2001; 286: 1340-1348.

Romero R, Espinoza J, Erez O, Hassan S. The role of cervical cerclage in obstetric practice: can the patient who could benefit from this procedure be identified? Am J Obstet Gynecol. 2006; 194: 1-9.

Romero R. Vaginal progesterone to reduce the rate of preterm birth and neonatal morbidity: a solution at last. Women's Health 2011; 7(5): 501-504.

Saigal S, Doyle L W. An overview of mortality and sequelae of preterm birth from infancy to adulthood. Lancet 2008; 371: 261-269.

Simcox R, Seed P T, Bennett P, Teoh T G, Poston L, Shennan A H. A randomized controlled trial of cervical scanning vs history to determine cerclage in women at high risk of preterm birth (CIRCLE trial). Am J Obstet Gynecol 2009; 200: 623.e1-6.

Souka A P, Heath V, Flint S, Sevastopoulou I, Nicolaides K H. Cervical length at 23 weeks in twins in predicting spontaneous preterm delivery. Obstet Gynecol 1999; 94: 450-454

To M S, Skentou C A, Royston P, Yu C K, Nicolaides K H. Prediction of patient-specific risk of early preterm delivery using maternal history and sonographic measurement of cervical length: a population-based prospective study. Ultrasound Obstet Gynecol 2006; 27: 362-367.

The invention claimed is:

1. A cervical pessary consisting of 20% to 30% w/w of progesterone homogenously distributed throughout 70% to 80% w/w of a dimethylsiloxane elastomer,
    wherein the dimethylsiloxane elastomer consists of:
    (A) a polydimethylsiloxane-vinyl polymer containing amorphous silica, and
    (B) a copolymer of dimethyl methylhydrogensiloxane and polydimethylsiloxane; having an A:B ratio ranging from 6:1 to 14:1,
    wherein the cervical pessary has a prolonged, sustained and continuous release of progesterone for a period of at least 6 months, and maintains its intact form all the time.

2. A cervical pessary according to claim 1, wherein the amount of progesterone in the pessary is from 5.0 g to 10.5 g.

3. A cervical pessary according to claim 1, having a weight between 25 and 35 grams.

4. A cervical pessary according to claim 1, wherein the amount of progesterone sustained and continuously released from the pessary is of 15 mg to 65 mg daily, for a period of at least 6 months.

5. A cervical pessary according to claim 1, wherein the A:B ratio is 6:1, 8:1, 10:1, 12:1 or 14:1.

6. A method for preventing preterm birth comprising administering the cervical pessary according to claim 1 to a patient in need thereof.

7. A cervical pessary according to claim 1, wherein:
    the polydimethylsiloxane-vinyl polymer (A) contains amorphous silica in an amount of 25% w/w of the polymer (A), and
    the copolymer (B) is a copolymer of 20% dimethyl methylhydrogensiloxane with polydimethylsiloxane.

8. A cervical pessary according to claim 7, wherein the amount of progesterone in the pessary is from 5.0 g to 10.5 g.

9. A cervical pessary according to claim 7, having a weight between 25 and 35 grams.

10. A cervical pessary according to claim 7, wherein the amount of progesterone initially released from the pessary is of 15 mg to 65 mg daily, for a period of at least 6 months.

11. A cervical pessary according to claim 7, wherein the A:B ratio is 6:1, 8:1, 10:1, 12:1 or 14:1.

12. A method for preventing preterm birth comprising administering the cervical pessary according to claim 7 to a patient in need thereof.

* * * * *